United States Patent [19]

Rowsell et al.

[11] 4,044,120

[45] Aug. 23, 1977

[54] COMPOUNDS HAVING A PHYSIOLOGICAL COOLING EFFECT, AND COMPOSITIONS CONTAINING THEM

[75] Inventors: David G. Rowsell, Staines; Roger Hems, Maidenhead, both of United Kingdom

[73] Assignee: Wilkinson Sword Limited, London, England

[21] Appl. No.: 568,663

[22] Filed: Apr. 16, 1975

[30] Foreign Application Priority Data

Apr. 17, 1974 United Kingdom ............... 16803/74

[51] Int. Cl.$^2$ .............................................. A61K 9/68
[52] U.S. Cl. ..................................... 424/48; 252/110; 424/45; 424/47; 424/49; 424/73; 424/322; 426/534; 426/650
[58] Field of Search ................... 424/322, 48; 252/110

[56] References Cited

U.S. PATENT DOCUMENTS

| 2,795,610 | 6/1957 | Gerjovich | 424/322 |
|---|---|---|---|
| 3,177,115 | 4/1965 | Casely et al. | 424/322 |
| 3,223,721 | 12/1965 | Martin et al. | 424/322 |
| 3,686,303 | 8/1972 | Knowles | 424/322 |
| 3,895,061 | 7/1975 | Richter | 424/322 |

*Primary Examiner*—Norman A. Drezin
*Attorney, Agent, or Firm*—Leydig, Voit, Osann, Mayer & Hoit, Ltd.

[57] ABSTRACT

Cyclic and acyclic amides, substituted ureas and sulphonamides are disclosed having the property of stimulating the cold receptors of the nervous system of the human body to produce a cold sensation and are used for this purpose in a variety of edible and topical preparations and in tobacco.

8 Claims, No Drawings

COMPOUNDS HAVING A PHYSIOLOGICAL COOLING EFFECT, AND COMPOSITIONS CONTAINING THEM

FIELD OF INVENTION

This invention relates to compositions and compounds having a physiological cooling effect on the skin and on the mucous membranes of the body, particularly those of the mouth, nose, throat and gastrointestinal tract.

BACKGROUND OF THE INVENTION AND PRIOR ART

Menthol is well known for its physiological cooling effect on the skin and mucous membranes of the mouth and has been extensively used as a flavouring agent (menthol being a major constituent of oil of peppermint) in foodstuffs, beverages, dentifrices, mouthwashes etc. and as a component in a wide range of toiletries, liniments and lotions for topical application. Menthol is also a well known tobacco additive for producing a 'cool' sensation in the mouth when smoking.

It is well established that the 'cooling' effect of menthol is a physiological effect due to the direct action of menthol on the nerve endings of the human body responsible for the detection of hot or cold and is not due to latent heat of evaporation. It is believed that the menthol acts as a direct stimulus on the cold receptors at the nerve endings which in turn stimulate the central nervous system.

Although menthol is well established as a physiological coolant its use, in some compositions, is circumscribed by its strong minty odour and its relative volatility.

A few other compounds have been reported in the technical literature as having an odour of flavour similar to menthol and from time to time have been proposed as flavourants or odourants in a variety of topical and ingestible compositions. For example, Japanese Patent Publication No. 39-19627 reports that 3-hydroxymethyl p-menthane (methyl carbinol) has a flavour closely resembling that of 1-menthol and suggests its use as a flavourant in confectionery, chewing gum, and tobacco. In Swiss Pat. No. 484,032 certain saccharide esters of menthol are proposed as additives to tobacco. In French patent specification No. 1,572,332 N,N-dimethyl 2-ethylbutanamide is reported as having a minty odour and refreshing effect, and the minty odour of N,N-diethyl 2,2-dimethylpropanamide is also referred to. A similar effect is reported for N,N-diethyl 2-ethylbutanamide in Berichte 39, 1223, (1906). A minty odour has also been reported for 2,4,6-trimethylheptan-4-ol and 2,4,6-trimethyl hept-2-en-4-ol in Parfums-Cosmetiques-Savons, May 1956, pp. 17-20. The cooling effect of menthol and other related terpene alcohols and their derivatives has also been studied and reported in Koryo, 95, (1970) pp. 39–43. 2,3-p-menthane diol has also been reported as having a sharp cooling taste (Beilstein, Handbuch der Organischen Chemie, 4th Ed. (1923) vol. 6, p.744). Still other substituted p-menthanes having a physiological cooling effect are disclosed in German Offenlegungsschrift Nos. P 22 02 535, P 22 03 947, P 22 03 273 and P 22 05 255.

Despite this knowledge of other compounds having an odour and flavour similar to that of menthol, menthol is still extensively used in topicol, ingestible and other compositions notwithstanding the disadvantages mentioned above, namely its very strong odour and its relative volatility, and despite its high cost.

OBJECTS OF THE INVENTION

It is an object of the present invention to provide other compounds having a pronounced physiological cooling effect, in many cases more persistent than that obtained with menthol, without the attendant disadvantages of a strong minty odour.

It is a further object to provide compounds having a pronounced physiological cooling effect and being of relatively low volatility.

It is a further object of the present invention to provide ingestible, topical and other compositions capable of stimulating the cold receptors of the nervous system of the human body thereby to create a desirable 'cool' sensation, and a method of making them.

It is a yet further object of the present invention to provide a method of stimulating the cold receptors of the nervous system of the body to create a cool sensation.

A further object is to provide compounds having physiological activity which are inexpensive and easily synthesised from readily available starting materials.

Other objects will be apparent from the following detailed description of the invention.

SUMMARY OF INVENTION

The present invention is based on the discovery of a group of cyclic and acyclic amides, substituted ureas and sulphonamides which have a pronounced physiological cooling activity, but which are without the strong minty smell of menthol, and which are inexpensive and easily synthesised from readily available starting materials.

The compounds discovered in accordance with this invention may be represented by the formula:

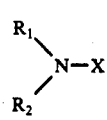

I where $R_1$, when taken separately, is H, $C_1$–$C_7$ alkyl or $C_3$–$C_6$ cycloalkyl;

$R_2$, when taken separately, is $C_3$–$C_8$ alkyl or $C_3$–$C_8$ alkylcycloalkyl, alkylcycloalkylalkyl, cycloalkyl, or cycloalkylalkyl, with the proviso that $R_2$ is branched at an alpha carbon atom relative to the N atom when $R_1$ is H or at an alpha or beta carbon atoms when $R_1$ is alkyl or cycloalkyl, this condition to be satisfied, in the case of cyclic groups, when the carbon atoms alpha or beta to the N atom is part of the cycle;

$R_1$ and $R_2$, when taken together, represent a straight or branched chain alkylene group forming with the N atom to which they are attached a 5–10 membered heterocycle, and preferably having branching at an alpha or beta carbon atom relative to the N atom;

$R_1$ and $R_2$ when separate groups and when taken together provide a total of at least 5 carbon atoms; and X represents $R_3CO-$, $R_4SO_2-$ or $R_5R_6NCO-$, where:

$R_3$ is H, $C_1$–$C_6$ alkyl, $C_3$–$C_6$ cycloalkyl, $C_2$–$C_8$ hydroxyalkyl, $C_2$–$C_8$ carboxyalkyl or $C_3$–$C_8$ alkylcarboxyalkyl, with the proviso that when $R_3$ is $C_6$ alkyl it is primary in structure;

$R_4$ is $C_1$-$C_6$ alkyl or $C_3$-$C_6$ cycloalkyl, with the proviso that when $R_4$ is $C_5$ or $C_6$ alkyl it is primary in structure.

$R_5$ and $R_6$, when taken separately, are each H, $C_1$-$C_6$ alkyl, $C_3$-$C_6$ alkylcycloalkyl, cycloalkyl, or cycloalkylalkyl, $C_2$-$C_8$ hydroxyalkyl, $C_2$-$C_8$ carboxyalkyl or $C_3$-$C_8$ alkylcarboxyalkyl; or together represent a straight or branched chain $C_3$-$C_{10}$ alkylene group optionally containing an ether oxygen atom; and where:

$R_1$, $R_2$ and X provide a total of from 7-16 carbon atoms.

STATEMENT OF INVENTION

In accordance with the invention, therefore, there are provided consumer products for application to or consumption by the human body into which there is incorporated a means for stimulating the cold receptors of the nervous system of the human body wherein said means comprise an effective amount of one or more compounds of the formula hereinbefore set forth.

by consumer products we mean a manufactured product applied to or consumed by the human person for toilet, cosmetic, hygienic, nutritive, curative, prophylactic, or other purposes and constituting a vehicle by means of which the said compounds may be brought into contact with the skin, mucous membranes or other surface tissues of the body, whether external tissues or internal, for example, of the nose, throat, mouth and gastrointestinal tract, and includes liquid and solid phase preparations of as essentially formless nature e.g. solutions, emulsions, pastes, ointments, powders etc., solid phase preparations of semi-permanent form, e.g. shaped toilet and cosmetic preparations and shaped edible preparations, whose shaped form is only temporary and which lose that form on use, and articles of permanent form but which are of an essentially disposable nature, e.g. cleansing tissues, toothpicks, etc.

Typical consumer products into which the compounds of this invention may be incorporated and which may therefore serve as vehicles for application of the compounds to the person are:

1. Edible and potable compositions including alcoholic and non-alcoholic beverages; confectionery, chewing gum, cachous; ice cream; jellies;
2. Toiletries including after-shave lotions, shaving soaps, creams and foams, toilet water, deodorants and antiperspirants, "solid colognes", toilet soaps, bath oils and salts, shampoos, hair oils, talcum powders, face creams, hand creams, sunburn lotions, cleansing tissues, dentifrices, toothpicks, mouthwashes, hair tonics, eye-drops;
3. Medicaments including antiseptic ointments, pile ointments, liniments, lotions, decongestants, counter-irritants, cough mixtures, throat lozenges, antacid and indigestion preparations, and analgesics;
4. Miscellaneous compositions such as water soluble adhesive compositions for envelopes, postage stamps, adhesive labels etc.
5. Tobacco and tobacco-containing preparations, e.g. cigarettes, pipe tobacco, chewing tobacco, snuff, cigars etc.

DETAILED DESCRIPTION

The compounds of formula I useful as cold receptor stimulants in accordance with this invention fall into three classes: cyclic and acyclic amides, i.e. compounds of formula I, where X is $R_3CO—$; substituted ureas, i.e. compounds of formula I where X is $R_5R_6NCO—$; and sulphonamides, i.e. compounds of formula I where X is $R_4SO_2—$. Of the three classes, the substituted ureas and the cyclic and acyclic amides are much to be preferred over the sulphonamides by reason of generally higher levels of physiological cooling activity, greater stability and cheaper manufacture. By reason of high levels of activity and cheapness, the substituted ureas are generally to be preferred over the cyclic and acyclic amides. The three classes of active compound will be discussed separately.

SUBSTITUTED UREAS

Broadly speaking the compounds of highest activity are the substituted ureas which may be represented by the formula II;

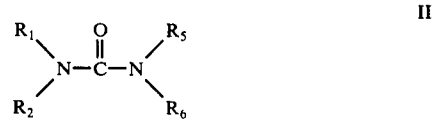

where $R_1$, $R_2$, $R_5$ and $R_6$ are as defined above. Preferred substituted ureas are those compounds where $R_1$ is H or $C_1$-$C_7$ alkyl, $R_2$ is $C_3$-$C_8$ alkyl or $C_3$-$C_8$ cycloalkyl, cycloalkylalkyl or alkylcycloalkyl, $R_2$ having branching in an alpha position relative to the N atom when $R_1$ is H, or at an alpha or beta position when $R_1$ is alkyl, or where $R_1$ and $R_2$ are joined to form an alkylene group having up to 10 carbon atoms and having branching at an alpha or beta position relative to the N atom, and forming together with the nitrogen atom a 5- to 6- 7- membered ring; and where $R_5$ is H or $C_1$-$C_6$ alkyl and $R_6$ is $C_1$-$C_6$ alkyl, or $C_3$-$C_6$ cycloalkyl, or where $R_5$ and $R_6$ jointly represent an alkylene group, optionally containing an ether oxygen atom and forming with the N atom a 5- or 6-membered ring.

The substituted ureas of formula II may be easily prepared by reaction of an appropriate amine with an isocyanate or carbamoyl chloride, the following being a typical reaction scheme:

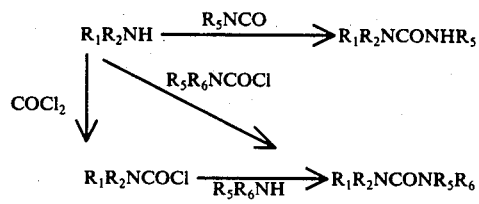

CYCLIC AND ACYCLIC AMIDES

The cyclic and acyclic amides useful in this invention may be represented by formula III:

where $R_1$, $R_2$ and $R_3$ are as defined above in connection with formula I. Preferred values for $R_1$ and $R_2$ are as set out above for formula II and the preferred values for $R_3$ are H, $C_1$-$C_6$ alkyl, $C_2$-$C_6$ hydroxyalkyl, carboxyalkyl or alkylcarboxyalkyl and $C_3$-$C_6$ cycloalkyl.

The amides may readily be prepared by reaction of the appropriate acid chloride and a substituted amine in accordance with procedures well known for the preparation of amides e.g.

$R_1R_2NH + R_3COCl \rightarrow R_1R_2NCOR_3$

CYCLIC AND ACYCLIC SULPHONAMIDES

Although less preferred than the substituted ureas and amides hereinbefore described, but nevertheless still possessing utility in the compositions of this invention, are sulphonamides of formula IV:

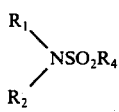

$$\begin{array}{c} R_1 \\ \diagdown \\ \diagup \\ R_2 \end{array} NSO_2R_4 \qquad IV$$

where $R_1$, $R_2$ and $R_4$ are as above defined in connection with formula I. Preferred values of $R_1$ and $R_2$ are as defined above in connection with formula II, whilst the preferred values for $R_4$ are $C_1$-$C_4$ alkyl.

The sulphonamides of formula IV may readily be prepared from the corresponding sulfonyl chloride and substituted amine by procedures well known in the art. e.g.

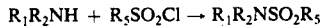
$R_1R_2NH + R_5SO_2Cl \rightarrow R_1R_2NSO_2R_5$

As will be apparent from the above formulae some of the compounds used as cold receptor stimulants in accordance with this invention exhibit either geometric or optical isomerism or both and, depending on the starting materials and the methods used in their preparation the compounds may be isometrically pure, i.e. consisting of one geometric or optical isomer, or they may be isometric mixtures, both in the geometric and optical sense. Generally, the compounds will be used as isomeric mixtures, but in some cases the cooling effect may differ as between geometric or optical isomers, and therefore one or other isomer may be preferred.

For the purposes of the present disclosure the following test procedure has been devised as a means to identify compounds having a physiological cooling activity in accordance with the present invention and herein referred to as cold receptor stimulants. This test is intended purely as a means for identifying compounds having a physiological cooling activity and useful in the present invention and for giving an indication of the different relative activities of the compounds, as between themselves and as compared with methanol, when applied in a particular manner to a particular part of the body. The results are not necessarily indicative of the activity of these compounds in other formulations and other parts of the body where other factors come into play. For example, a controlling factor in the onset of cooling effect, its intensity and longevity will be the rate of penetration of the compounds through the epidermis and this will vary in different locations on the human body. The formulation of actual products according to this invention will therefore be done largely on an empirical basis although the test results and other figures given herein will be useful as a guide, particularly in the formulation of products for oral administration, since the test procedure to be described involves oral application of the compound. A similar test may, of course, be devised for the purposes of measuring the relative activities of the compounds on another area of the body, for example, the face or forearm, and this will be a useful guide in the choice of compounds to be used in preparations for external topical usage.

It will also be noted that the described test procedure is done on a statistical basis. This is necessary since sensitivity to these compounds will vary not only from compound to compound and from one part of the body to another, but also from one individual to another. Tests of this nature are commonly used in the testing of the organoleptic properties, e.g. taste, smell etc. of organic and inorganic compounds, see Kirk-Othmer: Encyclopedia of Chemical Technology, 2nd Ed. (1967) Vol. 14, pages 336–344.

TEST PROCEDURE

The following test procedure is aimed at determining the minimum quantity of the test compound required to produce a noticeable cooling effect in a person of average sensitivity, this minimum quantity being termed the threshold for that particular compound. The tests are carried out on a selected panel of 6 people of median sensitivity to l-methanol.

PANEL SELECTION

To select a test panel of average sensitivity the following procedure is used. Known quantities of l-menthol in solution in petroleum ether (bp. 40–60) are placed on 5 mm. squares of filter paper, whereafter the solvent is allowed to evaporate. A panel of observers is enrolled and asked to place one impregnated square at a time on the tongue and to report on the presence or absence of a cooling effect. The quantity of l-menthol on each impregnated square is gradually reduced from a value substantially above 0.25 μg. per square to substantially below 0.25 μg. the precise range being immaterial. Conveniently, one startswith squares containing 2.0μg l-methol, the amount on each successive square being half that of the preceding square, i.e. the second test square will contain 1.0 μg. the third 0.5 μg, and so on. Each quantity is tested on the tongue at least 10 times. In this way, the thresholds to cold receptor stimulus by l-menthol are determined for each individual of the panel, the threshold for each individual being that amount of l-menthol for which, in a series of not less than 10 test applications, a cooling effect is reported 50% of the time. Six panel members are now selected whose threshold is approximately 0.25 μg, this select panel being regarded as the test panel of average sensitivity.

COMPOUND TESTING

To test the activity of compounds according to this invention, the above procedure is repeated using only the 6 selected panel members of average sensitivity to l-menthol. The individual thresholds for each test compound on each of the 6 selected panel members are determined and averaged. Those compounds whose average threshold on the select test panel is 100 μg or less are regarded as having cooling activity in accordance with this invention.

TEST RESULTS

The following tables set out the relative cooling activities of compounds of the formula defined above when tested according to the foregoing procedure.

Table I $$\begin{array}{c}R_1\\ \phantom{R_1}\diagdown\\ \phantom{R_1}N\\ \phantom{R_1}\diagup\\ R_2\end{array}\begin{array}{c}O\\ \|\\ C\end{array}\begin{array}{c}R_5\\ \diagup\\ N\\ \diagdown\\ R_6\end{array}$$

| Compound | | | | Activity | |
|---|---|---|---|---|---|
| $R_1$ | $R_2$ | $R_5$ | $R_6$ | bp. or mp. (° C) | μg |
| sec-$C_4H_9$— | sec-$C_4H_9$— | H— | $C_2H_5$— | 98–102°/ 0.2 mm | 1 |
| sec-$C_4H_9$— | sec-$C_4H_9$— | H— | $CH_3$— | 87–90° (m.p.) | 1.5 |
| n-$C_4H_9$— | t-$C_4H_9$ | H— | $C_2H_5$— | 90–92°/ 0.2 mm. | 1 |
| iso-$C_3H_7$— | iso-$C_3H_7$— | $C_2H_5$— | H— | 88–92°/ 0.8 mm | 5 |
| n-$C_5H_{11}$— | iso-$C_3H_7$— | H— | iso-$C_3H_7$— | 96°/ 0.35 mm. | 1.5 |
| iso-$C_3H_7$— | cyclo$C_6H_{11}$— | $CH_3$— | $CH_3$— | 82–85°/ 0.5 mm. | 3 |
| iso-$C_4H_9$— | iso-$C_4H_9$— | $CH_3$— | $CH_3$— | 63–65°/ 0.5 mm | 3 |
| iso-$C_4H_9$— | $(CH_3)_2CHCH(CH_3)$— | H— | $C_2H_5$— | 100–106°/ 0.4 mm | 1.5 |
| iso-$C_4H_9$ | iso-$C_4H_9$— | H— | $C_2H_5$— | 99–103°/ 0.2 mm | 10 |
| —$CH(CH_3)CH_2CH_2CH_2CH(CH_3)$— | | $C_2H_5$— | $C_2H_5$— | 91–3° (mp) | 10 |
| H— | $(CH_3)_3CCH_2C(CH_3)_2$— | H— | $C_2H_5$— | 100°/ 0.2 mm (sublimed) | 8 |
| cyclo$C_6H_{11}$— | iso-$C_3H_7$— | H— | $C_2H_5$— | 104–5° (mp) | 8 |
| —$CH(CH_3)CH_2CH_2CH(CH_3)$— | | " | " | 100–3°/ 0.6 mm | 10 |
| n-$C_4H_9$— | t-$C_4H_9$ | iso-$C_3H_7$— | H— | 81–4°/ 0.5 mm | 6 |
| H— | $(CH_3)_3CCH_2C(CH_3)_2$— | $C_2H_5$— | $C_2H_5$— | 98–100°/ 1.0 mm | 20 |
| —$CH(CH_3)CH_2CH_2CH_2CH(CH_3)$— | | H— | iso-$C_3H_7$— | 110–2°/ 0.5 mm | 11 |
| cyclo$C_6H_{11}$— | iso-$C_3H_7$— | " | " | 125–7°/ 0.5 mm | 12 |
| H— | $(CH_3)_3CCH_2C(CH_3)_2$— | " | " | 136–9°/ 0.5 mm | 10 |
| iso-$C_4H_9$ | iso-$C_4H_9$— | H— | n-$C_3H_7$— | 108–9°/ 0.3 mm | 20 |
| —$CH(CH_3)CH_2CH_2CH_2CH(CH_3)$— | | " | n-$C_4H_9$— | 129–31°/ 0.4 mm | 30 |
| —$CH(CH_3)CH_2CH_2CH(CH_3)$— | | " | " | 112–4°/ 0.1 mm | 30 |
| —$CH(CH_3)CH(C_2H_5)CH(CH_3)CH_2$— | | " | n-$C_3H_7$— | * | 20 |
| sec-$C_4H_9$— | sec-$C_4H_9$— | " | $C_2H_5OCOCH_2$— | * | 12 |
| " | " | " | $HOCH_2CH_2$— | * | 10 |
| " | " | " | H— | 68–71° (mp) | 20 |
| —$CH_2(CH_2)_6CH_2$— | | " | iso-$C_3H_7$— | 100–110°/ 0.01 mm | 7 |
| $C_2H_5$ | $CH(CH_3)_2CH_2CH(CH_3)$— | " | " | 80–81°/ (mp) | 7 |
| H | $CH(iso-C_3H_7)_2$— | " | n-$C_3H_7$— | 83–86°/ (mp) | 15 |
| —$CH_2CH_2CH(CH_3)CH_2CH_2CH$— | (iso$C_3H_7$)— | " | $C_2H_5$— | 106–10°/ 0.1 mm | 4 |
| iso-$C_3H_7$— | (cyclo $C_7H_{13}$)$CH_2$— | " | " | 122–6°/ 0.005 mm | 20 |
| $CH(CH_3)_2CH_2CH(CH_3)$— | $CH(CH_3)_2CH_2CH(CH_3)$— | H— | $C_2H_5$— | 88–90°/ 0.001 mm | 20 |
| sec.-$C_4H_9$— | iso-$C_4H_9$— | " | iso$C_3H_7$— | 57–60° (mp) | 2 |
| $C_2H_5$— | $CH(CH_3)_2CH(CH_3)$— | " | " | 47–50° (mp) | 8 |
| n-$C_3H_7$— | $CH(C_2H_5)_2$— | " | $C_2H_5$— | 81–3°/ 0.005 mm | 4 |
| cyclo$C_5H_9$— | iso-$C_4H_9$— | " | " | 108–10°/ 0.005 mm | 3 |
| sec.$C_4H_9$— | (cyclo $C_6H_{11}$)$CH_2$— | " | " | 106–9°/ 0.005 mm | 20 |
| n-$C_3H_7$— | (1'-methylcyclo$C_6H_{10}$) $CH_2$— | " | " | 112–4°/ 0.005 mm | 15 |
| cyclo$C_5H_9$— | $CH_3CH_2CH_2CH(CH_3)$— | " | n-$C_3H_7$ | 120–1°/ 0.6 mm | 8 |
| (iso-$C_3H_7)_2CH$— | (Cyclo-$C_3H_5$)$CH_2$— | " | $C_2H_5$— | 95–110°/ 0.01 mm | 5 |
| $C_2H_5$— | $(CH_3)_2CHCH(CH_3)$— | " | $HO(CH_2)_6$— | — | 20 |
| " | " | n-$C_3H_7$— | n-$C_3H_7$— | 64–6°/ 0.01 mm | 5 |
| $C_2H_5$— | $(CH_3)_2CHCH(CH_3)$— | —$CH_2CH_2OCH_2$— | | 64–5°/ 0.005 mm | 1 |
| " | " | —$CH_2CH_2CH_2CH_2$— | | 75–6°/ 0.005 mm | 0.5 |
| H | $CH_3CH_2C(CH_3)_2$— | H | iso-$C_3H_7$— | 170–2° (mp) | 10 |

Table I-continued $$\begin{array}{c} R_1 \quad O \quad R_5 \\ \diagdown \parallel \diagup \\ N-C-N \\ \diagup \quad \diagdown \\ R_2 \quad R_6 \end{array}$$

| Compound | | | | Activity | |
|---|---|---|---|---|---|
| R₁ | R₂ | R₅ | R₆ | bp. or mp. (° C) | μg |
| C₂H₅— | (C₂H₅)₂CH | " | " | 64–6° (mp) | 3 |
| " | " | " | Cyclo-C₃H₅— | 89–91°/0.02 mm | 0.4 |
| " | " | " | n-C₆H₁₃— | 118–9°/0.005 mm | 3 |
| " | " | CH₃— | HOCH₂CH₂— | 88–92°/0.01 mm | 6 |
| iso-C₄H₉— | sec.C₄H₉— | H | (cyclo-C₅H₉)CH₂— | 124–7°/0.3 mm | 3 |
| " | " | " | (3'-methyl)-CycloC₅H₈— | 106–110°/0.45 mm | 10 |
| iso-C₃H₇— | iso-C₃H₇— | " | cycloC₆H₁₁— | 94–5° (mp) | 8 |
| Sec.C₄H₉— | Sec-C₄H₉ | H | CycloC₆H₁₁— | 80–81° (mp) | 10 |

*Compounds not distilled, but were tested in a crude state.

Table II $$\begin{array}{c} R_1 \quad O \\ \diagdown \parallel \\ NC-R_3 \\ \diagup \\ R_2 \end{array}$$

| Compound | | | Activity | |
|---|---|---|---|---|
| R₁ | R₂ | R₃ | bp or mp (° C) | μg |
| sec-C₄H₉— | sec-C₄H₉— | C₂H₅— | 65–6°/0.2 mm | 2 |
| —CH(CH₃)CH₂CH₂CH₂CH(CH₃)— | | " | 77°/0.5 mm | 3 |
| H— | (CH₃)₃CCH₂C(CH₃)₂— | " | 88–100°/0.5 mm (sublimed) | 5 |
| sec-C₄H₉— | sec-C₄H₉— | n-C₄H₉— | 75–6°/0.18 mm | 4 |
| " | " | CH₃— | 53–6°/0.1 mm | 2 |
| iso-C₄H₉— | (CH₃)₂CHCH(CH₃)— | " | 68–72°/0.5 mm | 2 |
| —CH(CH₃)CH₂CH₂CH₂CH(CH₃)— | | t-C₄H₉— | 123–4°/12 mm | 2 |
| H— | (CH₃)₃CCH₂C(CH₃)₂— | iso-C₃H₇— | 93–5°(mp) | 2 |
| sec-C₄H₉— | sec-C₄H₉— | " | 61–2°/0.01 mm | 5 |
| n-C₅H₁₁— | iso-C₃H₇— | C₂H₅— | 68°/0.35 mm | 3 |
| cycloC₆H₁₁— | iso-C₃H₇— | CH₃— | 131–3°/12 mm | 8 |
| sec-C₄H₉— | sec-C₄H₉— | iso-C₃H₇— | 111–2°/11 mm | 6 |
| —CH(CH₃)CH₂CH₂CH₂CH(CH₃)— | | " | 134–8°/12 mm | 6 |
| iso-C₃H₇— | iso-C₃H₇— | C₂H₅ | 42–6°/0.02 mm | 8 |
| H— | (CH₃)₃CCH₂C(CH₃)₂— | iso-C₄H₉— | 80–90°/0.5 mm (Sublimed) | 7 |
| " | " | t-C₄H₉— | 83–5°/mp. | 5 |
| " | " | H— | 81–7°/0.3 mm | 8 |
| n-C₄H₉— | t-C₄H₉— | C₂H₅— | 62–4°/0.2 mm | 6 |
| —CH(CH₃)CH₂CH₂CH(CH₃)— | | iso-C₃H₇— | 46–8°/0.01 mm | 6 |
| iso-C₄H₉— | iso-C₄H₉— | C₂H₅— | 65–7°/0.15 mm | 12 |
| —CH(CH₃)CH₂CH₂CH₂CH(CH₃)— | | n-C₄H₉— | 81–5°/0.35 mm | 12 |
| " | | H— | 59–63°/0.2 mm | 11 |
| H— | (CH₃)₃CCH₂C(CH₃)₂— | n-C₄H₉— | 92°/0.15 mm | 20 |
| H— | C₂H₅CH(CH₃)CH₂CH(CH₃)— | C₂H₅— | 146–7°/15 mm | 18 |
| iso-C₃H₇— | cycloC₆H₁₁— | n-C₃H₇— | 69–73°/.003 mm | 11 |
| —CH(CH₃)CH₂CH₂CH₂CH(CH₃)— | | CH₃— | 71–4°/0.5 mm | 25 |
| n-C₄H₉— | t-C₄H₉— | iso-C₄H₉ | 75–6°/0.2 mm | 40 |
| sec-C₄H₉— | sec-C₄H₉— | H— | 56–8°/0.2 mm | 10 |
| —CH(CH₃)CH₂CH₂CH₂CH(CH₃)— | | iso-C₄H₉— | 81–6°/0.2 mm | 6 |
| sec.-C₄H₉— | iso-C₄H₉— | n-C₃H₇— | 60°/0.002 mm | 2 |
| " | " | H— | 70–2°/2.0 mm | 4 |
| C₂H₅— | CH(CH₃)₂CH(CH₃)— | iso-C₃H₇— | * | 2 |
| n-C₃H₇— | (C₂H₅)₂CH— | C₂H₅— | 60–2°/0.02 mm | 5 |
| cycloC₅H₉— | iso-C₄H₉— | " | 89°/0.5 mm | 6 |
| sec-C₄H₉— | (cyclo-C₆H₁₁)CH₂— | CH₃— | 72–4°/0.003 mm | 15 |
| CH₃— | (CH₃)₃CCH₂C(CH₃)₂— | C₂H₅— | 55–7°/0.01 mm | 3 |
| sec.C₄H₉— | cycloC₇H₁₃— | " | 83–5°/0.02 mm | 9 |
| (isoC₃H₇)₂CH— | (cycloC₃H₅)CH₂— | cyclo-C₄H₇— | 88–92°/0.005 mm | 6 |
| iso-C₃H₇— | iso-C₄H₉— | n-C₆H₁₃— | 90–2°/0.2 mm | 4 |
| H— | (CH₃)₂CH(CH₂)₃CH(CH₃)— | " | 136–41°/0.2 mm | 20 |
| C₂H₅— | (CH₃)₂CHCH(CH₃)— | HO(CH₂)₅— | 120–5°/0.01 mm | 8 |
| iso-C₃H₇— | iso-C₃H₇— | C₂H₅OOC(CH₂)₄— | 104–9°/0.01 mm | 4 |
| " | " | HOOC(CH₂)₄— | 150–70°/0.7 mm | 30 |
| C₂H₅ | CH(CH₃)₂CH₂CH(CH₃)— | C₂H₅— | 52–3°/0.01 mm | 2 |
| sec.C₄H₉— | sec.-C₄H₉— | cyclo C₆H₁₁— | 86–7°/0.005 mm | 9 |
| —CH(CH₃)CH₂CH₂CH₂CH(CH₃)— | | " | 120–6°/0.01 mm | 15 |
| H | (isoC₃H₇)₂CH— | iso C₃H₇— | 130–1°/m.p. | 3 |
| H | (CH₃)₃CCH₂C(CH₃)₂— | cyclo C₆H₁₁— | 114–6°/m.p. | 40 |
| —CH₂CH₂CH(CH₃)CH₂CH₂CH | (iso C₃H₇)— | CH₃— | 73–4°/0.15 mm | 3 |
| C₂H₅— | CH(CH₃)₂CH(CH₃)— | C₂H₅OOC(CH₂)₄— | 107–8°/0.001 mm | 20 |

Table II-continued $$\begin{array}{c} R_1 \\ \diagdown \\ \diagup \\ R_2 \end{array} NC\!-\!R_3 \quad \begin{array}{c} O \\ \| \\ \end{array}$$

| Compound | | | Activity | |
|---|---|---|---|---|
| R₁ | R₂ | R₃ | bp or mp (° C) | μg |
| iso-C₃H₇— | (cyclo C₇H₁₃)CH₂— | C₂H₅— | 106-8°/0.5 mm | 20 |
| sec. C₄H₉— | sec.C₄H₉— | (CH₃)₃CCH₂— | 74-75°/0.3 mm | 5 |
| C₂H₅— | CH(CH₃)₂CH(CH₃)— | " | 68-9°/0.4 mm | 6 |
| iso-C₄H₉— | " | cyclo C₃H₅— | 70°/0.2 mm | 4 |
| n-C₃H₇— | (C₂H₅)₂CH— | cyclo C₄H₇— | 78.5-80°/0.1 mm | 4 |
| C₂H₅— | iso C₄H₉— | " | 63-4°/0.2 mm | 3 |
| —CH(CH₃)CH₂CH₂CH₂CH(CH₃)— | | cyclo C₃H₅— | 77-82°/0.2 mm | 2 |
| " | | cyclo C₄H₇— | 80°/0.25 mm | 2 |
| | | cyclo C₅H₉— | 103-7°/0.6 mm | 5 |
| iso C₃H₇— | iso C₄H₉— | cyclo C₃H₅— | 55°/0.005 mm | 2 |
| " | " | cyclo C₅H₉— | 101-3°/2 mm | 3 |
| —CH₂(CH₂)₆CH₂— | | C₂H₅— | 59°/0.005 mm | 7 |
| sec. C₄H₉— | (cyclo C₃H₅)CH₂— | " | 58-9°/0.01 mm | 3 |
| (CH₃)₂CHCH₂CH(CH₃)— | (CH₃)₂CHCH₂CH(CH₃)— | CH₃— | 58-9°/0.01 mm | 10 |
| H | (iso C₃H₇)₂CH— | cyclo C₃H₅— | 136-8°/mp. | 4 |

*Not distilled, tested crude

Table III $$\begin{array}{c} R_1 \\ \diagdown \\ \diagup \\ R_2 \end{array} NSR_4 \quad \begin{array}{c} O \\ \| \\ \end{array}$$

| Compound | | | Activity | |
|---|---|---|---|---|
| R₁ | R₂ | R₄ | .p. ° C | μg |
| sec-C₄H₉— | sec-C₄H₉— | CH₃— | 90-3°/0.7 mm | 1 |
| iso-C₃H₇— | iso-C₃H₇— | C₂H₅— | 84-6°/0.3 mm | 8 |
| CH(CH₃)CH₂CH₂CH₂CH(CH₃)— | | " | 98-100°/0.3 mm | 7 |
| C₂H₅— | (CH₃)₂CHCH(CH₃)— | " | 93-4°/0.4 mm | 8 |
| —CH(CH₃)CH(C₂H₅)CH(CH₃)CH₂— | | " | 106-7°/0.4 mm | 6 |
| iso-C₃H₇— | cycloC₆H₁₁— | " | 109-115°/0.3 mm | 10 |
| H— | (CH₃)₃CCH₂C(CH₃)₂— | " | 115-8°/0.3 mm | 20 |
| —CH₂CH(C₂H₅)CH₂CH₂CH(CH₃)— | | CH₃— | 107-9°/0.3 mm | 15 |
| iso-C₃H₇— | iso-C₄H₉— | n-C₃H₇— | 74-6°/0.005 mm | 9 |
| C₂H₅— | iso-C₄H₉— | n-C₅H₁₁— | 95-8°/0.15 mm | 9 |

UTILITY

The cold receptor stimulants used in this invention find utility in a wide variety of consumer products for consumption by or application to the human body. Broadly speaking, these products can be divided into ingestibles and topicals, both terms being taken in their broadest possible sense. Thus ingestible is to be taken as including not only foodstuffs and beverages taken into the mouth and swallowed, but also other orally ingested products taken for reasons other than their nutritional value, e.g. indigestion tablets, antacid preparations, laxatives, etc. Ingestible is also to be taken to include edible compositions taken by mouth, but not necessarily swallowed, e.g. chewing gum. Topical is to be taken as including not only compositions such as perfumes, powders and other toiletries, lotions, liniments, oils and ointments, applied to the external surfaces of the human body, whether for medical or other reasons, but also compositions applied to, or which, in normal usage, come in contact with, internal mucous membranes of the body, such as those of the nose, mouth, or throat, whether by direct or indirect application, mouthwash and gargle compositions. Topical products, in this context, also include toilet articles such as cleansing tissues and toothpicks.

In formulating the products of this invention the cold receptor stimulants will be incorporated into a vehicle by means of which the compound may be applied to the person. THe vehicle may, itself be completely inert or it may, as usually will, contain other active ingredients. A wide variety of vehicles will be suitable, depending upon the particular product involved, such vehicles including solids, liquids, emulsions, foams and gels. Typical vehicles for the cold receptor stimulants include aqueous or alcoholic solutions, oils and fats such as hydrocarbon oils, fatty acid esters, long chain alcohols and silicon oils; finely divided solids such as starch or talc; cellulosic materials such as paper tissue; low-boiling hydrocarbons and halohydrocarbons used as aerosol propellants; gums and natural or snythetic resins.

Generally, these vehicles will contain at least one or more of the following adjuvants: flavourants, colourants, perfuming agents, surface active agents, antiseptic agents, such as are usually employed in topical and ingestible compositions.

A more detailed discussion of particular products according to this invention follows.

TOILETRIES AND COSMETICS

A major area of utility of the cold receptor stimulants of this invention will be in the field of toilet preparations broadly classed as personal care products. These may be defined as manufactured products applied to the person for the purposes of grooming or hygiene or for cosmetic purposes, including make up and perfumery, but excluding ethical and proprietary medical preparations. Particular personal care products are discussed hereinafter by way of example and are illustrated hereinafter in the specific examples.

One class of personal care products into which the compounds of this invention may be incorporated is represented by lotions for topical application, e.g. after-shave lotions, toilet water, etc. where the compound will be used in alcoholic or aqueous alcoholic solution, such solutions usually also containing a perfume or mild antiseptic or both. The amount of compound added to the formulation will usually be in the range of 0.1 to 2.5% by weight based on the total composition.

Another class of personal care product is represented by soap and soap-based compositions where the compounds will be used in combination with an oil or fat or a natural or synthetic surfactant e.g. a fatty acid salt or a laurylsulphate salt, the composition usually also containing an essential oil or perfume. The range of soap compositions will include soaps of all kinds e.g. toilet soaps, shaving soaps, shaving foams etc. particularly shaving foams of the aerosol type. Usually the compound will be added to the formulation in amount of from 0.5 to 2.5% by weight.

A further class of personal care products into which the cold receptor stimulants may be incorporated is represented by cosmetic creams, emollients and lotions, such creams, emollients and lotions usually comprising an oil-in-water emulsion as a base and optionally containing a range of other ingredients such as wax, preservative, perfume, antiseptics, astringents, pigments etc. Also included within this class are lipstick compositions, such compositions usually comprising an oil and wax base into which the coolant can be incorporated along with other ingredients e.g. pigments. Once again the formulation of such products, apart from the incorporation of the cold receptor stimulant, usually in an amount by weight of from 0.1 to 2.5%.

Personal care products for oral hygiene into which the cold receptor stimulants of this invention can be incorporated include mouthwash, gargle and dentifrice compositions. The first two may be considered together and will usually comprise an aqueous, alcoholic or aqueous-alcoholic solution of an antiseptic often coloured or flavoured for palatability, to which the cold receptor stimulant is added in an amount of from 0.1 to 1.0% by weight.

Dentifrice compositions may be of the solid block, powder, paste or liquid type and will usually comprise a finely divided abrasive or polishing material, e.g. precipitated chalk, silica, magnesium silicate, aluminum hydroxide or other similar materials well known in the art, and a detergent or foaming agent. Optional ingredients which may also be included are flavouring agents and colourants, antiseptics, lubricants, thickeners, emulsifiers or plasticizers. The amount of cold receptor stimulant added in such compositions will generally be from 0.1 to 2.0% by weight based on the total composition.

EDIBLE AND POTABLE COMPOSITIONS

The cold receptor stimulants of this invention may be incorporated into a wide range of edible and potable compositions comprising an edible or potable base and usually one or more flavoring or colouring agents. The particular effect of the cold receptor stimulant is to create a cool or fresh sensation in the mouth, and in some cases, even in the stomach, and therefore the compounds find particular utility in sugar-based confectionery such as chocolate, boiled sweets, mints and candy, an ice cream and jellies and in chewing gum. The formulation of such confections will be traditional techniques and according to conventional recipes and as such forms no part of this invention. The cold receptor stimulant will be added to the recipe at a convenient point and in amount sufficient to produce the desired cooling effect in the final product. As already indicated, the amount will vary depending upon the particular compound, the degree of cooling effect desired and the strength of other flavourants in the recipe. For general guidance, however, amounts in the range 0.1 to 1.0% by weight based on the total composition will be found suitable.

Similar considerations apply to the formulation of beverages. Generally speaking the compounds will find most utility in soft drinks, e.g. fruit squashes, lemonade, cola etc., but may also be used in alcoholic beverages. The amount of compound will generally be in the range 0.01 to 1.0% by weight based on the total composition.

MEDICAMENTS

Because of their cooling effect on the skin and on the mucous membranes of the mouth, throat and nose and of the gastrointestinal tract the cold receptor stimulants may be used in a variety of oral medicines, nasal and throat sprays, and topical compositions, particularly where a counter-irritant is required. Generally speaking, these medical preparations, whether topical or ingestible, proprietary or ethical, will contain a pharmaceutically acceptable carrier, either liquid or solid, a pharmaceutically active ingredient and into these preparations the cold receptor stimulants of this invention can readily be incorporated to provide a pleasant cooling effect on the skin, or other surface tissues of the body, or in the mouth or gastrointestinal tract depending on particular preparation and whether it is to be applied externally or internally. A particular utility for the compounds of this invention is in the formulation of antacid and indigestion remedies, and especially those based on sodium bicarbonate, magnesium oxide, calcium or magnesium carbonate, aluminium or magnesium hydroxide or magnesium trisilicate. In such compositions the compound will usually be added in an amount of from 0.1 to 2.0%.

The cold receptor stimulants may also be included in oral analgesic compositions, e.g. with acetyl salicyclic acid or its salts, and in nasal decongestants e.g. those containing ephedrine.

Consumer products according to the invention are illustrated by the following Examples in which all percentages are by weight.

EXAMPLE 1

After-Shave Lotion

An after-shave lotion was prepared according to the following recipe by dissolution of the ingredients in the liquid and cooling and filtering:

| | |
|---|---|
| Denatured ethanol | 75% |
| Diethylphthalate | 1.0% |
| Propylene Glycol | 1.0% |
| Lactic Acid | 1.0% |
| Perfume | 3.0% |
| Water | to 100% |

Into the base lotion was added 0.5% by weight of N-ethyl-N',N'-di-sec-butyl urea.

When the final solution was applied to the face a clearly noticeable cooling effect became apparent after a short interval of time.

EXAMPLE 2

Antiseptic Ointment

An ointment was prepared according to the following formulations:

| | |
|---|---|
| Cetyltrimethyl ammonium bromide | 4.0% |
| Cetyl Alcohol | 6.0% |
| Stearyl Alcohol | 6.0% |
| White Paraffin | 14.0% |
| Mineral Oil | 21.0% |
| Water | to 100% |

The ingredients were mixed, warmed to 40° C and emulsified in a high speed blender. Added to the mixture during blending was 1.5% of N,N-dimethyl-N'-cyclohexyl-N'-isopropyl urea.

The final ointment when applied to the skin gave rise to a cooling effect.

EXAMPLE 3

Cleansing Tissue

A cleansing liquid was prepared having the formulation:

| | |
|---|---|
| Triethanolamine Lauryl sulphate | 1.0% |
| Glycerol | 2.0% |
| Perfume | .95% |
| Water | to 100% |

To this liquid was added 1.0% of N-ethyl-N'-n-butyl-N'-t-butyl urea. A paper tissue was then soaked in the liquid.

When the impregnated tissue was used to wipe the skin a fresh cool sensation developed on the skin after a short interval.

EXAMPLE 4

Toothpaste

The following ingredients were mixed in a blender:

| | |
|---|---|
| Dicalcium phosphate | 48.0% |
| Sodium lauryl sulphate | 2.5% |
| Glycerol | 24.8% |
| Sodium carboxymethyl cellulose | 2.0% |
| Citrus flavourant | 1.0% |
| Sodium saccharin | 0.5% |
| Water | to 100% |

Shortly before completion of the blending operation 1.0% by weight of N-(2,2-dimethylpropionyl)-2,6-dimethylpiperidine was added to the blender.

When applied as a toothpaste a pleasant cooling effect is noticed in the mouth.

EXAMPLE 5

Aerosol Shaving Soap

An aerosol shaving soap composition was formulated according to the following recipe:

| | |
|---|---|
| Stearic Acid | 6.3% |
| Lauric Acid | 2.7% |
| Triethanolamine | 4.6% |
| Sodium Carboxymethyl Cellulose | 0.1% |
| Sorbitol | 5.0% |
| Water | to 100% |
| Perfume | 0.5% |

The composition was prepared by fusing the acids in water, adding the triethanolamine, cooling and adding the other constituents. To the mixture was then added 0.5% of N,N-di-sec-butyl-propionamide.

The composition was then packaged in an aerosol dispenser under pressure of a butane propellant.

When used in shaving a fresh cool sensation was noticed on the face.

EXAMPLE 6

Soft Drink

A soft drink concentrate was prepared from the following recipe:

| | |
|---|---|
| Pure orange juice | 60% |
| Sucrose | 10% |
| Saccharin | 0.2% |
| Orange flavouring | 0.1% |
| Citric acid | 0.2% |
| Sulphur dioxide | trace amount |
| Water | to 100% |

To the concentrate was added 0.10% of N-(2,4,4-trimethylpent-2-yl)-2-methylpropionamide.

The concentrate was diluted with water and tasted. An orange flavour having a pleasantly cool after-effect was obtained.

EXAMPLE 7

Toothpick

The tip of a wooden toothpick was impregnated with an alcoholic solution containing N,N-di-sec-butyl methanesulphonamide in an amount sufficient to deposit on the toothpick 0.05 mg of the compound. The toothpick was then dried.

When placed against the tongue a cool sensation is noticed after a short period of time.

EXAMPLE 8

After Shave Lotion

After shave lotion was prepared according to the following recipe by dissolution of the ingredients in the liquid and cooling and filtering:

| | |
|---|---|
| Denatured ethanol | 75% |
| Diethylphthalate | 1.0% |
| Propylene Glycol | 1.0% |
| Lactic Acid | 1.0% |
| Perfume | 3.0% |
| Water | to 100% |

Into a sample of the base lotion was added 0.7% by weight based on the weight of the sample of N-propionyl-2,6-dimethylpiperidine.

When the final solution was applied to the face a clearly noticeable cooling effect became apparent after a short interval of time.

EXAMPLE 9

Cleansing Tissue

A cleansing liquid was prepared having the formulation:

| | |
|---|---|
| Triethanolamine Lauryl sulphate | 1.0% |
| Glycerol | 2.0% |
| Perfume | .95% |
| Water | to 100% |

To this liquid was added 1% of N-isobutyl-N-sec.butyl butanamide. A paper tissue was then soaked in the liquid.

When the impregnated tissue was used to wipe the skin a fresh cool sensation developed on the skin after a short interval.

EXAMPLE 10

Toothpaste

The following ingredients were mixed in a blender:

| | |
|---|---|
| Dicalcium phosphate | 48.0% |
| Sodium lauryl sulphate | 2.5% |
| Glycerol | 24.8% |
| Sodium carboxymethyl cellulose | 2.0% |
| Citrus flavourant | 1.0% |
| Sodium saccharin | 0.5% |
| Water | to 100% |

Shortly before completion of the blending operation 1% by weight of N-n-pentyl-(N,N')diisopropylurea was added to the blender.

When applied as a toothpaste a pleasant cooling effect is noticed in the mouth.

EXAMPLE 11

Aerosol Shaving Soap

An aerosol shaving soap composition was formulated according to the following recipe:

| | |
|---|---|
| Stearic acid | 6.3% |
| Lauric acid | 2.7% |
| Triethanolamine | 4.6% |
| Sodium carboxymethyl cellulose | 0.1% |
| Sorbitol | 5.0% |
| Water | to 100% |
| Perfume | 0.5% |

The composition was prepared by fusing the acids in water, adding the triethanolamine, cooling and adding the other constitutents. To the mixture was then added 0.7% of N-isobutyl-N'-ethyl-N-(1,2-dimethyl-n-propyl)urea. The composition was then packaged in an aerosol dispenser under pressure of a butane propellant.

EXAMPLE 12

Toothpaste

The following ingredients were mixed in a blender:

| | |
|---|---|
| Dicalcium phosphate | 48.0% |
| Sodium lauryl sulphate | 2.5% |
| Glycerol | 24.8% |
| Sodium carboxymethyl cellulose | 2.0% |
| Citrus flavourant | 1.0% |
| Sodium saccharin | 0.5% |
| Water | to 100% |

Shortly before completion of the blending operation 1.5% by weight of N,N-diisopropyl ethanesulphonamide was added to the blender.

When applied as a toothpaste a pleasant cooling effect is noticed in the mouth.

EXAMPLE 13

Aerosol Shaving Soap

An aerosol shaving soap composition was formulated according to the following recipe:

| | |
|---|---|
| Stearic acid | 6.3% |
| Lauric acid | 2.7% |
| Triethanolamine | 4.6% |
| Sodium carboxymethyl cellulose | 0.1% |
| Sorbitol | 5.0% |
| Water | to 100% |
| Perfume | 0.5% |

The composition was prepared by fusing the acids in water, adding the triethanolamine, cooling and adding the other constituents. To the mixture was then added 1.0% of N-isobutyl-N-isopropyl propanesulphonamide. The composition was then packaged in an aerosol dispenser under pressure of a butane propellant.

When used in shaving a fresh cool sensation is distinctly noticeable on the face.

EXAMPLE 14

Hair Shampoo

Sodium lauryl ether sulphate, 10 g., was dispersed in 90 g. water in a high speed mill. To the dispersion was added 2% by weight of N-n-butyl-N,N'-di-sec.-butylurea. When the hair is washed using the shampoo a fresh, cool sensation is noticed on the scalp.

EXAMPLE 15

Toothpick

The tip of a wooden toothpick was impregnated with an alcoholic solution containing N'-[N-ethyl-N-(1,2-dimethyl-n-propyl)carbamoyl]pyrrolidine, in an amount sufficient to deposit on the toothpick 0.05 mg. of the compound. The toothpick was then dried.

When placed against the tongue a cool sensation is noticed after a short period of time.

EXAMPLE 16

Soft Drink

A soft drink concentrate was prepared from the following recipe:

| | |
|---|---|
| Pure orange juice | 60% |
| Sucrose | 10% |
| Saccharin | 0.2% |
| Orange flavouring | 0.1% |
| Citric acid | 0.2% |
| Sulphur dioxide | Trace amount |
| Water | to 100% |

To the concentrate was added 0.2% of N,N-di-sec.butyl ethanesulphonamide.

The concentrate was diluted with water and tasted. An orange flavour having a pleasantly cool after-effect was obtained.

EXAMPLE 17

Toilet Water

A toilet water was prepared according to the following recipe:

| | |
|---|---|
| Denatured ethanol | 75.0% |

| | |
|---|---|
| Perfume | 5.0% |
| Water | to 100% |

The the recipe was added 2.0% based on the total composition, of N,N-di-sec.butyl methanesulphonamide.

As with the after-shave lotions, a cooling effect was clearly noticeable on the skin well after the termination of any cooling effect attributable to the evaporation of the alcoholic carrier.

EXAMPLE 18

Soft Sweet

Water was added to icing sugar at 40° C to form a stiff paste. 0.2% of N-n-propyl-N-(1-ethyl-n-propyl)-N'-cyclopropylurea was then stirred into the paste and the mixture allowed to set. A soft sweet mass resulted having the characteristic cooling effect in the mouth of peppermint but without the minty flavour or odour.

EXAMPLE 19

Hydrophilic Ointment

A hydrophilic ointment was prepared having the following formulation:

| | |
|---|---|
| Propylene Glycol | 12% |
| 1-Octadecanol | 25% |
| White soft paraffin | 25% |
| Sodium lauryl sulphate | 1% |
| Water | to 100% |

The sodium lauryl sulphate was added to the water and heated to 60° C. The paraffin was melted by heating to 60° C and was then added to the sodium lauryl sulphate mixture with stirring. Propylene glycol and 1-octadecanol was then added to this mixture.

To the resultant mixture was added 1.5% of N-isobutyl-N-sec.butyl formamide.

The final ointment was applied to the skin gave rise to a marked cooling effect.

EXAMPLE 20

Deodorant Composition

A deodorant composition suitable for formulation and dispensing as an aerosol under pressure of a suitable propellant was formulated according to the following recipe:

| | |
|---|---|
| Denatured ethanol | 96.9% |
| Hexachlorophene | 2.0% |
| Isopropyl myristate | 1.0% |
| Perfume | 0.1% |

To the composition was added 2% by weight of N-isobutyl-N'-ethyl-N-cyclopentyl urea. Application of the final composition gave rise to a definite cooling sensation on the skin.

EXAMPLE 21

Lipstick 1.0% by weight of N-ethyl-N-(1,2-dimethyl-n-propyl)-6-hydroxyhexanamide was incorporated into a proprietary lipstick by melting the lipstick, adding the compound, and allowing the lipstick to resolidify. When applied to the lips a persistent cooling effect is clearly noticeable.

EXAMPLE 22

Solid Cologne

A solid cologne was formulated according to the following recipe:

| | |
|---|---|
| Denatured ethanol | 74.5% |
| Propylene glycol | 3.0% |
| Sodium stearate | 5.0% |
| Perfume | 5.0% |
| Water | to 100% |

The sodium stearate was dissolved by stirring in a warm mixture of the ethanol, propylene glycol and water. To the solution was added the perfume and 2% of N-isopropyl-N-isobutyl cyclopentanecarboxamide, and the mixture then allowed to solidify into a waxy cake.

When applied to the forehead a strong cooling effect was obtained.

EXAMPLE 23

Hair Tonic

A hair tonic was formulated containing:

| | |
|---|---|
| Denatured ethanol | 84.5% |
| Castor Oil | 14.0% |
| Resorcinol | 0.5% |
| Perfume | 1.0% |

The castor oil, resorcinol and perfumes were dissolved in the ethanol component and to the solution was added 2% of N-ethanesulphonyl-2,6-dimethylpiperidine. When rubbed on the scalp a cooling effect is noticed.

EXAMPLE 24

Mouthwash

A concentrated mouthwash composition was prepared according to the following recipe:

| | |
|---|---|
| Ethanol | 3.0% |
| Borax | 2.0% |
| Sodium bicarbonate | 1.0% |
| Glycerol | 10.0% |
| Flavourant | 0.4% |
| Thymol | 0.03% |
| Water | to 100% |

To the composition was added 0.1% of N-methyl-N-2-hydroxyethyl-N'-n-propyl-N'-(1'-ethyl-n-propyl) urea.

When diluted with approximately 10 times its own volume of water and used to rinse the mouth a strong cooling effect is obtained in the mouth.

EXAMPLE 25

Talcum Powder

A talcum powder was prepared by grinding together the following:

| | |
|---|---|
| Low micron talc | 90% |
| Zinc stearate | 5% |
| Starch | 5% |

In the course of grinding there was added 1.0% of N-sec.butyl-N-isobutyl-N'-isopropylurea. A talcum powder having a freshening and cooling effect was obtained.

EXAMPLE 26

Chewing Gum

Leaves of a proprietary chewing gum were leached in running water for 168 hours to remove all water-soluble flavourants. At the end of the leaching operation the chewing gum base had no detectable minty odour or flavour. The chewing gum base was then kneaded with 0.5% of N-[N'-ethyl-N'-(1,2-dimethyl-n-propyl)carbamoyl]morpholine. When compared with the water-extracted chewing gum base, the final product showed no distinguishable change in flavour but showed a marked cooling effect in the mouth.

EXAMPLE 27

Toilet Water

A toilet water was prepared according to the following recipe:

| | |
|---|---|
| Denatured ethanol | 75.0% |
| Perfume | 5.0% |
| Water | to 100% |

The the recipe was added 1.0% based on the total composition, of N-[N'-ethyl-N'-(1,2-dimethyl-n-propyl)carbamoyl]pyrrolidine. As with the after-shave lotion, a cooling effect was clearly noticeable on the skin well after the termination of any cooling effect attributable to the evaporation of the alcoholic carrier.

EXAMPLE 28

Soft Sweet

Water was added to icing sugar at 40° C to form a stiff paste. 0.2% of N-cyclohexyl-N-isopropylacetamide was then stirred into the paste and the mixture allowed to set. A soft sweet mass resulted having the characteristic cooling effect in the mouth of peppermint but without the minty flavour or odour.

EXAMPLE 29

Hydrophilic Ointment

A hydrophilic ointment was prepared having the following formulation:

| | |
|---|---|
| Propylene Glycol | 12% |
| 1-Octadecanol | 25% |
| White soft paraffin | 25% |
| Sodium lauryl sulphate | 1% |
| Water | to 100% |

The sodium lauryl sulphate was added to the water and heated to 60° C. The paraffin was melted by heating to 60° C and was then added to the sodium lauryl sulphate mixture with stirring. Propylene glycol and 1-octadecanol was then added to this mixture.

To the resultant mixture was added 1.5% of N,N-di-sec.butyl ethanesulphonamide.

The final ointment when applied to the skin gave rise to a marked cooling effect.

EXAMPLE 30

Deodorant Composition

A deodorant composition suitable for formulation and dispensing as an aerosol under pressure of a suitable propellant was formulated according to the following recipe:

| | |
|---|---|
| Denatured ethanol | 96.9% |
| Hexachlorophene | 2.0% |
| Isopropyl myristate | 1.0% |
| Perfume | 0.1% |

To the composition was added 1% by weight of N,N-di-sec.butyl methanesulphonamide. Application of the final composition gave rise to a definite cooling sensation on the skin.

EXAMPLE 31

Lipstick 1.0% by weight of N-isobutyl-N-sec.butyl-N'-cyclopentylurea was incorporated into a proprietary lipstick by melting the lipstick, adding the compound, and allowing the lipstick to resolidify. When applied to the lips a persistent cooling effect is clearly noticeable.

EXAMPLE 32

Solid Cologne

A solid cologne was formulated according to the following recipe:

| | |
|---|---|
| Denatured ethanol | 74.5% |
| Propylene glycol | 3.0% |
| Sodium stearate | 5.0% |
| Perfume | 5.0% |
| Water | to 100% |

The sodium stearate was dissolved by stirring in a warm mixture of the ethanol, propylene glycol and water. To the solution was added the perfume and 1.0% of N,N-diisobutyl-N',N'-dimethylurea, and the mixture then allowed to solidify into a waxy cake.

When applied to the forehead a strong cooling effect is obtained.

EXAMPLE 33

Hair Tonic

A hair tonic was formulated containing:

| | |
|---|---|
| Denatured ethanol | 84.5% |
| Castor Oil | 14.0% |
| Resorcinol | 0.5% |
| Perfume | 1.0% |

The castor oil, resorcinol and perfumes were dissolved in the ethanol component and to the solution was added 1.0% of N-(2,2-dimethylpropionyl)-2,6-dimethylpiperidine. When rubbed on the scalp a cooling effect is noticed.

EXAMPLE 34

Mouthwash

A concentrated mouthwash composition was prepared according to the following recipe:

| | |
|---|---|
| Ethanol | 3.0% |
| Borax | 2.0% |

-continued

| | |
|---|---|
| Sodium bicarbonate | 1.0% |
| Glycerol | 10.0% |
| Flavourant | 0.4% |
| Thymol | 0.03% |
| Water | to 100% |

To the composition was added 0.1% of N-(2,4,4-trimethylpent-2-yl)-2-methylpropionamide. When diluted with approximately 10 times its own volume of water and used to rinse the mouth a strong cooling effect is obtained in the mouth.

EXAMPLE 35

Talcum Powder

A talcum powder was prepared by grinding together the following

| | |
|---|---|
| Low micron talc | 90% |
| Zinc stearate | 5% |
| Starch | 5% |

In the course of grinding there was added 2% of N-(2,4-dimethylpent-3-yl)-2-methylpropionamide. A talcum powder having a freshening and cooling effect was obtained.

EXAMPLE 36

Chewing Gum

Leaves of a proprietary chewing gum were leached in running water for 168 hours to remove all water-soluble flavourants. At the end of the leaching operation the chewing gum base had no detectable minty odour or flavour. The chewing gum base was then kneaded with 0.05% of N-n-propyl-N-(1-ethyl-n-propyl)cyclobutanecarboxamide. When compared with the water-extracted chewing gum base, the final product showed no distinguishable change in flavour but showed a marked cooling effect in the mouth.

The above Examples illustrate the range of compounds and the range of compositions included within the present invention. However, they are not to be taken as limiting the scope of the invention in any way. Numerous other compounds within the general formula will be equally suitable for use in the compositions of Examples 1–36 and the physiological cooling effect obtained with the compounds of the invention will recommend their use in a wide variety of other compositions where the cooling effect will be of value.

The substituted ureas, amides and sulphonamides hereinbefore referred to as cold receptor stimulants in ingestible and topical compositions also find utility as cold receptor stimulants in tobacco and tobacco-containing manufactures.

As has already been mentioned, menthol is extensively used for this purpose notwithstanding its strong minty odour and relative volatility. Other similar compounds have also been proposed as alternatives to menthol in tobacco, see for example, the various publications hereinbefore referred to. Still other compounds have been proposed as 'flavourants' in tobacco rather than 'coolants' and amongst these may be mentioned 2-isopropyl-5-methyl hexanol (alternatively named 2,6-dimethylhept-3-yl methanol) and related compounds as disclosed in U.S. Pat. No. 3,704,714. Notwithstanding these various disclosures a need still exists for alternatives to menthol for incorporating into tobacco to provide a 'tool' effect when smoked.

It is a further object of the present invention, therefore, to provide tobacco and tobacco-containing manufactures containing an ingredient which creates a 'cool' sensation when the ingredient comes into contact with the nasal and oral mucosa, either in the tobacco smoke, or by direct contact of the tobacco on the nasal or oral mucosa, but which are not subject to the disadvantages of a strong minty flavour and storage instability.

It is a yet further object of the present invention to provide an improved method of imparting to tobacco and tobacco-containing manufactures a physiological cooling activity.

According to the present invention, therefore, there are also provided tobacco and tobacco-containing manufactures comprising tobacco and a cold receptor stimulating additive, present in an amount effective to stimulate the cold receptors of the nervous system of mucous membranes of the oral and nasal mucosa when the tobacco or tobacco-containing manufacture is smoked, chewed or inhaled by the human user, said additive being a cold receptor stimulating compound of formula (I) hereinbefore defined.

By tobacco and tobacco-containing manufactures we mean any article, such as cigarette or cigar, or any composition, such as pipe or chewing tobacco or snuff, containing tobacco in a prepared form ready for utilisation by the human person whether by smoking, i.e. burning of the prepared tobacco and inhalation of the tobacco smoke, chewing or direct inhalation of the tobacco.

In formulating the tobacco and tobacco-containing manufactures of this invention the active compound may be incorporated directly into the tobacco, for example, by impregnation of the tobacco with an alcholic solution of the active ingredient, at a suitable stage of manufacture. However, in an alternative and preferred arrangement the active ingredient may be incorporated into a tobacco smoke filter for use in a pipe or cigarette filter or as a filter tip for cigarettes. The latter, in particular, forms a particularly effective utilisation of the present invention, the active compound simply being impregnated in the wad of material forming the filter tip. This may be of any of the well known types of filter tip for cigarettes, e.g. a filter pad of cellulose acetate, paper, cotton, α-cellulose or asbestos fiber. Conveniently the filter tip is impregnated with an alcoholic solution of the active compound and then dried to deposit the active compound therein.

The amount of active compound to be incorporated into the tobacco or tobacco-containing manufacture in accordance with the invention will vary from compound to compound depending on the activity thereof, i.e. the amount thereof which it is necessary to place in contact with the skin to produce a noticeable cooling effect, and will depend also on the mode of application thereof, i.e. whether the compound is impregnated in the tobacco itself, or in a filter tip or in any other accessory. However, the actual amount is not critical to this invention and will be readily determinable by the person skilled in the art by means of a few simple tests. As a matter of guidance, however, it may be mentioned that with the more active compounds, as little as 0.1 mg. deposited on the filter tip of a tipped cigarette is effective.

This latter aspect of the invention is illustrated by the following Examples.

EXAMPLE 37

Cigarette Tobacco

A proprietary brand of cigarette tobacco was sprayed with an ethanolic solution of N,N-di-isobutyl-N',N'-dimethyl urea and was rolled into cigarettes each containing approximately 0.5 mg. of active compound. Smoking the impregnated cigarettes produced a cool effect in the mouth characteristic of mentholated cigarettes but without any attendant odour other than that normally associated with tobacco.

Impregnation of the filter tip of a proprietary brand of tipped cigarette with 0.5 mg. of N,N-di-secbutyl acetamide produced a similar effect.

EXAMPLE 38

Cigarette Tobacco

A proprietary brand of cigarette tobacco was sprayed with an ethanolic solution of N-(2,4,4-trimethylpent-2-yl) propionamide and was rolled into cigarettes each containing approximately 0.5 mg. of active compound. Smoking the impregnated cigarettes produced a cool effect in the mouth characteristic of mentholated cigarettes.

EXAMPLE 39

Filter Tip Cigarette

The filter tip of a proprietary brand of cigarette was impregnated with an ethanol solution of N,N-disec. butyl methanesulphonamide in an amount sufficient to deposit in the filter 0.5 mg. of the active compound. Smoking the cigarette with the impregnated tip gave rise to a noticeable cooling effect in the mouth.

EXAMPLE 40

Pipe Tobacco

A proprietary brand of pipe tobacco was sprayed with an ethanolic solution of N-n-butyl-N-t-butyl-N'-ethylurea. 2g. of the tobacco containing 0.5 mg. of the active compound was placed in a pipe. Smoking the impregnated tobacco produced a cool effect in the mouth characteristic of mentholated tobacco but without any attendant odour other than that normally associated with tobacco.

EXAMPLE 41

Cigars

The tobacco of a proprietary brand of cigar was impregnated with an ethanolic solution of N-(1,3-dimethylbutyl)-N-ethylpropionamide in an amount sufficient to deposit in the cigar 0.5 mg. of the active compound. Smoking the cigar with the impregnated tobacco gave rise to a noticeable cooling effect in the mouth.

EXAMPLE 42

Chewing Tobacco

A proprietary brand of chewing tobacco was impregnated with an ethanolic solution of N-acetyl-2,6-dimethyl-piperidine. 1g. of the tobacco containing 0.2 mg. of active compound was used. Chewing the impregnated tobacco produced a cool effect in the mouth.

EXAMPLE 43

Snuff

A proprietary brand of snuff was impregnated with an ethanolic solution of N-isobutyl-N-sec.butyl-N'-isopropylurea. 1g. of the snuff was impregnated with 5 mg. of active compound. About 0.01 g. of the impregnated snuff produced a cool effect in the nose when inhaled.

EXAMPLE 44

Cigarette Tobacco

A proprietary brand of cigarette tobacco was sprayed with an ethanolic solution of N,N-disec.butyl ethanesulphonamide and was rolled into cigarettes each containing approximately 0.5 mg. of active compound. Smoking the impregnated cigarettes produced a cool effect in the mouth characteristic of mentholated cigarettes but without any attendant odour other than that normally associated with tobacco.

EXAMPLE 45

Filter Tip Cigarette

The filter tip of a proprietary brand of cigarette was impregnated with an ethanolic solution of N-[N'-ethyl-N'-(1,2-dimethyl-n-propyl)carbamoyl]pyrrolidine in an amount sufficient to deposit in the filter 0.5 mg. of the active compound. Smoking the cigarette with the impregnated tip gave rise to a noticeable cooling effect in the mouth.

We claim:

1. In a manufactured consumer product for application to or consumption by the human body, said product comprising (a) a topically administrable or orally ingestible vehicle and one or more of the following: a flavorant, colorant, odorant, surfactant or antiseptic, and (b) a compound capable of stimulating the cold receptors of the nervous system in the surface tissues of the body when brought into contact therewith, the improvement which comprises using as the cold receptor stimulating compound an effective amount of a cold receptor stimulating urea of the formula:

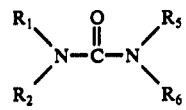

wherein $R_1$ is H, $C_1$-$C_7$ alkyl or $C_3$-$C_6$ cycloalkyl;

$R_2$ is $C_3$-$C_8$ alkyl or $C_3$-$C_8$ cycloalkyl, alkylcycloalkyl, cycloalkylalkyl or alkylcycloalkylalkyl, with the proviso that when $R_1$ is H then $R_2$ is branched at an alpha carbon atom relative to the N atom, or at an alpha or beta carbon atom when $R_1$ is alkyl or cycloalkyl; and $R_5$ and $R_6$ are each H, $C_1$-$C_6$ alkyl, $C_3$-$C_6$ alkylcycloalkyl, cycloalkyl or cycloalkylalkyl, $C_2$-$C_8$ hydroxyalkyl, $C_2$-$C_8$ carboxyalkyl or $C_3$-$C_8$ alkylcarboxyalkyl;

$R_1$, $R_2$, $R_5$ and $R_6$ together providing a total of from 7–16 carbon atoms.

2. A product according to claim 1, which is a toilet lotion comprising an aqueous, alcoholic or aqueous-alcoholic base; an antiseptic, perfuming agent, colorant or mixture thereof; and said cold receptor stimulating compound.

3. A product according to claim 1, which is a cosmetic preparation comprising an oil-in-water emulsion cosmetic base; an antiseptic, perfuming agent, colorant or mixture thereof; and said cold receptor stimulating compound.

4. A product according to claim 1, which is a toilet soap, into which there is incorporated an effective amount of said cold receptor stimulating compound.

5. A product according to claim 1, which is a shaving soap, foam or cream into which there is incorporated an effective amount of said cold receptor stimulating compound.

6. A product according to claim 1, which is an edible or potable preparation comprising an edible or potable base; a flavorant on colorant or a mixture thereof, and an effective amount of said cold receptor stimulating compound.

7. A product according to claim 1, which is a chewing gum into which there is incorporated an effective amount of said cold receptor stimulating compound.

8. A method of stimulating the cold receptors of the nervous system of the human body which comprises applying thereto an effective amount of a cold receptor stimulating compound of the formula defined in claim 1.

* * * * *